US010976260B2

(12) United States Patent
Qin (10) Patent No.: US 10,976,260 B2
(45) Date of Patent: Apr. 13, 2021

(54) ELECTROCHEMILUMINESCENCE IMMUNOASSAY SYSTEM AND FLOW-THROUGH CELL COMPONENT THEREOF

(71) Applicant: BEIJING UNIDIAG TECHNOLOGY INC, Beijing (CN)

(72) Inventor: Jun Qin, Beijing (CN)

(73) Assignee: BEIJING UNIDIAG TECHNOLOGY INC, Beijing (CN)

( * ) Notice: Subject to any disclaimer, the term of this patent is extended or adjusted under 35 U.S.C. 154(b) by 248 days.

(21) Appl. No.: 15/771,441

(22) PCT Filed: Mar. 28, 2016

(86) PCT No.: PCT/CN2016/077481
§ 371 (c)(1),
(2) Date: Apr. 27, 2018

(87) PCT Pub. No.: WO2017/071154
PCT Pub. Date: May 4, 2017

(65) Prior Publication Data
US 2018/0335389 A1    Nov. 22, 2018

(30) Foreign Application Priority Data

Oct. 29, 2015    (CN) .......................... 201510717595.7

(51) Int. Cl.
*G01N 21/76* (2006.01)
*G01N 21/05* (2006.01)
(Continued)

(52) U.S. Cl.
CPC .............. *G01N 21/76* (2013.01); *G01N 21/05* (2013.01); *G01N 21/66* (2013.01); *G01N 27/403* (2013.01);
(Continued)

(58) Field of Classification Search
None
See application file for complete search history.

(56) References Cited

U.S. PATENT DOCUMENTS 5,466,416 A * 11/1995 Ghaed .................... G01N 21/69
422/52
5,643,721 A * 7/1997 Spring ................. G01N 33/543
435/6.16
(Continued)

FOREIGN PATENT DOCUMENTS

CN    205103164    3/1916
CN    102680456    9/2012
(Continued)

OTHER PUBLICATIONS

Machine translation of CN 104950026 to Soochow University, accessed Feb. 2020 at eSpacenet (original document provided by applicant in IDS dated Apr. 27, 2018) (Year: 2015).*
(Continued)

*Primary Examiner* — Jill A Warden
*Assistant Examiner* — Brittany I Fisher
(74) *Attorney, Agent, or Firm* — Parker Highlander PLLC (57) ABSTRACT

An electrochemiluminescence immunoassay system and a flow-through cell unit (1) thereof. The flow-through cell unit (1) comprises a working electrode (12), a counter electrode (11) and a reference electrode (13), wherein the working electrode (12) and the counter electrode (11) are vertically provided, and there is a liquid flow path between the two electrodes. When an electrochemical reaction occurs, and when reactants are evenly distributed on the working electrode (12) for a test. After the flow-through cell is cleaned, the liquid flow path is unblocked, so that the cleaning effect is better. A porous structure is provided on a connection surface where the reference electrode (13) is in communication with the liquid flow path, and the porous structure
(Continued)

makes the reference electrode (13) have a good electrical conductivity, and prevents the reference electrode (13) from early ageing, and improves the durability of the flow-through cell unit (1).

6 Claims, 5 Drawing Sheets

(51) Int. Cl.
*G01N 21/66* (2006.01)
*G01N 27/403* (2006.01)
*G01N 27/30* (2006.01)
*G01N 33/543* (2006.01)

(52) U.S. Cl.
CPC ... *G01N 33/54386* (2013.01); *G01N 2458/30* (2013.01)

(56) References Cited

U.S. PATENT DOCUMENTS

| | | | | |
|---|---|---|---|---|
| 5,705,402 | A | * | 1/1998 | Leland .................. C12Q 1/6825 436/518 |
| 6,051,392 | A | | 4/2000 | Ikeda et al. |
| 6,120,676 | A | * | 9/2000 | Heller .................. A61B 5/1411 205/775 |
| 6,200,531 | B1 | * | 3/2001 | Liljestrand ............. G01N 21/69 250/361 C |
| 6,312,910 | B1 | * | 11/2001 | Vellinger .................. C07K 1/24 435/6.13 |
| 7,695,601 | B2 | | 4/2010 | Jiang et al. |
| 10,302,641 | B2 | | 5/2019 | Nobuki et al. |
| 2008/0047332 | A1 | | 2/2008 | Kuhnl et al. |
| 2013/0189798 | A1 | | 7/2013 | Donnerbauer et al. |
| 2014/0072963 | A1 | | 3/2014 | Qin |

FOREIGN PATENT DOCUMENTS

| | | |
|---|---|---|
| CN | 202631475 | 12/2012 |
| CN | 203720142 | 7/2014 |
| CN | 204484303 | 7/2015 |
| CN | 104950026 | 9/2015 |
| JP | H 07-209189 A | 8/1995 |
| JP | H 11-352092 A | 12/1999 |
| JP | 2004-208777 A | 7/2004 |
| JP | 2006-090991 | 4/2006 |
| JP | 2008-051813 A | 3/2008 |
| JP | 2013-152215 A | 8/2013 |
| JP | 2014-153178 A | 8/2014 |

OTHER PUBLICATIONS

Machine translation of CN 204484303 to Jingjing, Tian, accessed Feb. 2020 at eSpacenet (original document provided by applicant in IDS dated Apr. 27, 2018) (Year: 2015).*

Machine translation of CN 202631475 to Guangzhou General Hospital of Guangzhou Military Command, accessed Feb. 2020 at eSpacenet (original document provided by applicant in IDS dated Apr. 27, 2018) (Year: 2012).*

English translation of Office Communication issued in Japanese Patent Application No. 2018-521855, dated Apr. 9, 2019.

PCT International Search Report issued in International Application No. PCT/CN2016/077481, dated Jul. 12, 2016.

* cited by examiner

ELECTROCHEMILUMINESCENCE IMMUNOASSAY SYSTEM AND FLOW-THROUGH CELL COMPONENT THEREOF

CROSS REFERENCE TO RELATED APPLICATIONS

This application is a national phase application under 35 U.S.C. § 371 of International Application No. PCT/CN2016/077481, filed on Mar. 28, 2016, which claims the priority of Chinese Patent Application No. 201510717595.7, filed on Oct. 29, 2015 with the State Intellectual Property Office of People's Republic of China, and titled with "ELECTROCHEMILUMINESCENCE IMMUNOASSAY SYSTEM AND FLOW-THROUGH CELL COMPONENT THEREOF", and the disclosures of each of which are hereby incorporated by reference.

FIELD

The present invention relates to the field of medical apparatus technology, specifically to an electrochemiluminescence immunoassay system and a flow-through cell unit thereof.

BACKGROUND

ECL (Electrochemiluminescence) refers to a chemical reaction produced by the reaction products on the electrode surface or between the reaction products on the electrode surface and some components in the system, after a constant voltage is applied to the electrode. The reaction process includes three stages: electrochemical reaction process, chemiluminescence and circulation process.

Electrochemiluminescence immunoassay technology is a combination of electrochemiluminescence (ECL) and immunoassay. The principle of its luminescence of marker is different from that of regular chemiluminescence (CL). It is a kind of specific chemiluminescence reaction initiated by electrochemical reaction on the electrode surface, which actually includes two processes: electrochemistry and chemiluminescence. The difference between ECL and CL is that ECL is a luminescence reaction initiated by electricity while CL is a luminescence reaction initiated by the mixed compounds.

ECL not only can be used in all of the immunoassays, but also can be used in DNA/RNA probe detection. It is a new generation of labeled immunoassay technology after radio immunoassay (MA), enzyme immunoassay (EIA), fluorescence immunoassay (FIA), chemiluminescence immunoassay. ECL technology is adapted to the principle of many kinds of immune reaction, and its unique advantage enables the development of a large amount of detection reagents relying on its platform, for more than 100 items such as hormones, thyroid function, tumor markers, myocardial markers, anemia, infectious diseases and so on.

At present, the container of the conventional electrochemiluminescence detector in which electrochemiluminescence reaction occurs mainly includes three types, i.e., reaction cell, reaction cup of a printed electrode, and flow cell.

Firstly, for electrochemiluminescence detector of which electrochemical reaction takes place in reaction cell, the reaction cell is not easy to be cleaned and reused. In addition, the reaction electrode, counter electrode and reference electrode of the detector are usually columnar, which is suitable for laboratory investigation with a small amount of assay, but not suitable for large-scale clinical assay.

Secondly, for electrochemiluminescence detector of which three electrodes are printed in the reaction cup, electrochemiluminescence reaction takes place on the three electrodes in the reaction cup. The reaction cup can only be used for once, and due to the relative high value of electrode material, the single-use cost is unduly high. In addition, the reference electrode should be immersed in liquid before and during use to best serve as a reference. The reaction cup of the printed electrode makes the reference electrode exposed in dry air, prone to being oxidized or aged.

Finally, for conventional electrochemiluminescence detector installed flow cell, working electrode of the flow cell is deposed in the center of the electrode pan, and counter electrode surrounds the working electrode at the periphery. These two electrodes are deposed on the same horizontal plane. When cleaning the flow cell with this structure, the cleaning liquid needs to cycle around the gaps between the working electrode and the counter electrode. The cleaning is hard to be carried out and the cleaning result is not good, making the two electrodes easy to be aged, affecting the accuracy of a measurement result and decreasing the service life of the flow cell.

In view of the disadvantages of the flow-through cell above, it is an urgent demand to provide a flow cell, which is reusable, of which the electrode is not easy to be aged, and which has accurate measurement results.

SUMMARY

In order to solve the technical problems above, the first object of the present disclosure is to provide a flow-through cell unit for electrochemiluminescence immunoassay system. In the flow-through cell unit, the counter electrode and the working electrode are arranged one above the other, which is convenient for cleaning the flow-through cell and has no dead angle, avoiding electrode aging caused by poor cleaning, and therefore improving the accuracy of measurement results dramatically.

The second object of the present disclosure is to provide an electrochemiluminescence immunoassay system which comprises the flow-through cell unit.

In order to achieve the first object of the present disclosure, the present disclosure provides a flow-through cell unit for electrochemiluminescence immunoassay system in which a test liquid undergoes electrochemiluminescence reaction, comprising a working electrode and a counter electrode, wherein the working electrode and the counter electrode are arranged one above the other.

In the present disclosure, the working electrode and the counter electrode are arranged one above the other. When the flow-through cell unit is cleaned, the cleaning liquid does not need to cycle around the two electrodes, making it convenient to clean and without dead angle, so that achieving a better cleaning result, avoiding the aging of electrode caused by poor cleaning, and greatly improving the accuracy of a measurement result.

Optionally, the counter electrode comprises two needle electrodes disposed above the working electrode, and the working electrode is a sheet electrode.

Optionally, the counter electrode and the working electrode are disposed in the flow-through cell unit, and the flow-through cell unit has a liquid flow path for liquid to flow through.

The flow-through cell unit further comprises a reference electrode disposed on one side of the flow-through cell unit, wherein the working electrode, the counter electrode and the reference electrode are in fluid communication through liquid flow path therebetween, and wherein the reference electrode comprises a third working section which is in fluid communication with the liquid flow path and its communication side with the liquid flow path is provided with a porous structure.

Optionally, the flow-through cell unit is formed by an upper plate and a lower plate matching each other, wherein the upper plate is made of transparent material, the counter electrode is fixed to the upper plate, and the working electrode is fixed to the lower electrode.

Optionally, a gasket having a first through hole is provided between the upper plate and the lower plate, wherein the first through hole, the lower plate and the upper plate form a reaction chamber, wherein a liquid inlet and a liquid outlet are provided in the lower plate under the reaction chamber, and wherein the test liquid undergoes electrochemiluminescence reaction in the reaction chamber.

Optionally, screw holes in communication with each other are provided in the upper plate, the gasket and the lower plate.

Optionally, the counter electrode comprises a first working section, the working electrode comprises a second working section, and the first working section and the second working section form a reaction circuit.

Optionally, at least one end of the first working section bends along the direction to the upper plate to form a first hook, a first hook groove matching the first hook is provided in the upper plate, and the first hook is clipped to the first hook groove;

at least one end of the second working section bends along the direction to the lower plate to form a second hook, a second through hole matching the second hook is provided on the lower plate, and the second hook is clipped to the second through hole.

In order to achieve the second aim of the present disclosure, the present disclosure provides an electrochemiluminescence immunoassay system, comprising a flow-through cell unit and an detection unit for detecting the flow-through cell unit, and further comprising a control unit for controlling the operation of the flow-through cell unit, and a fixing plate for fixing the flow-through cell unit and the control unit, wherein the flow-through cell unit is the flow-through cell unit mentioned above.

Optionally, the control unit comprises a rotating arm and a stepper motor; one end of the rotating arm is hinged to the stepper motor for controlling the rotation of the rotating arm; and the other end of the rotating arm is connected to a magnet for attraction of the magnetic beads in the test liquid to the working electrode.

In FIGS. 1 to 9:
1 flow-through cell unit, 11 counter electrode, 111 first working section, 112 first hook;
12 working electrode, 121 second hook, 122 second working section;
13 reference electrode, 131 housing of the reference electrode, 132 third working section;
14 upper plate, 15 lower plate, 151 second through hole;
16 gasket, 161 first through hole, 162 arc structure, 17 groove;
2 control unit, 21 rotating arm, 22 stepper motor, 23 magnet;
3 detection unit, 4 fixing plate.

DETAILED DESCRIPTION

In order to help one of ordinary skill in the art to understand the technical solution of the present disclosure better, the present disclosure will be further illustrated in conjunction with the attached figures and examples hereinafter.

Figure 1:
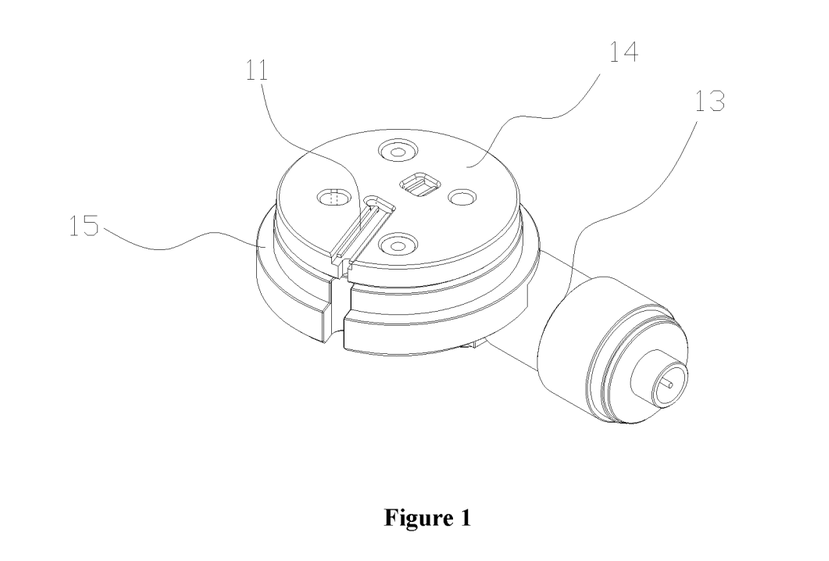
FIG. 1 is the structure representation of the flow-through cell unit.
Figure 2:
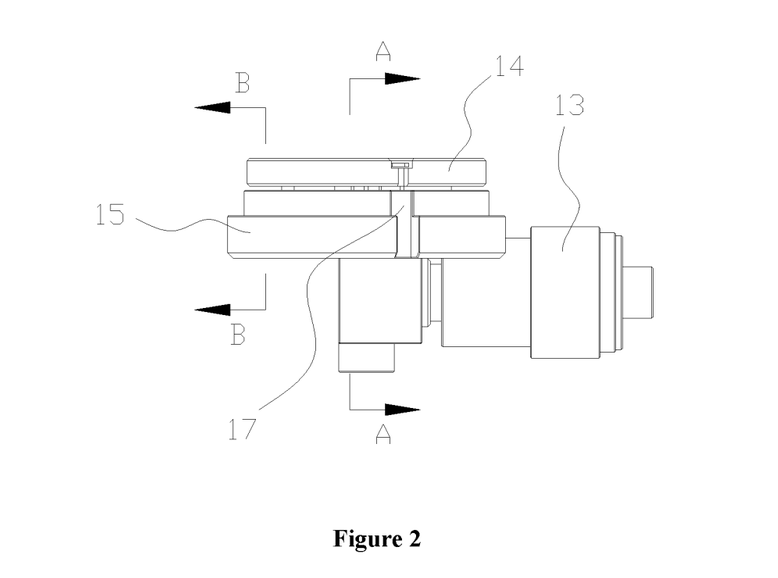
FIG. 2 is a front view of FIG. 1.
Figure 3:
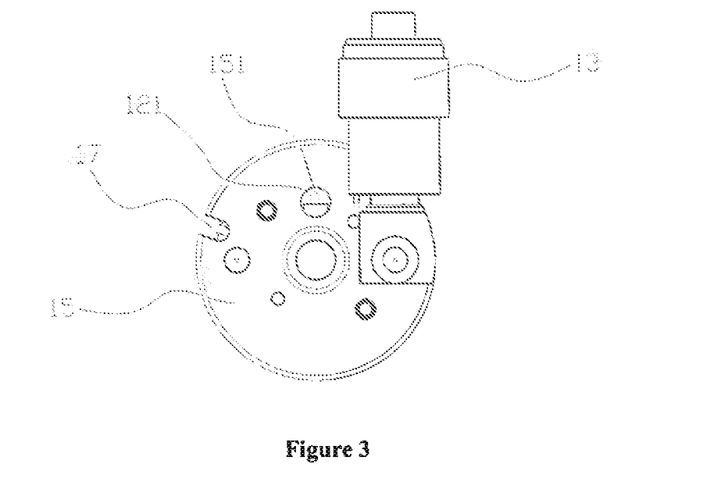
FIG. 3 is a bottom view of FIG. 1.
Figure 4:
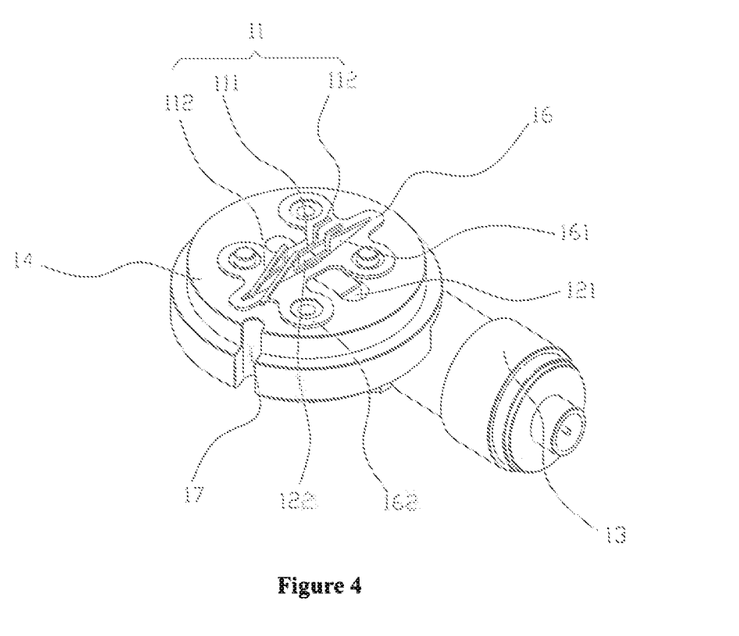
FIG. 4 is a structure representation of FIG. 1 after the upper plate is removed.
Figure 5:
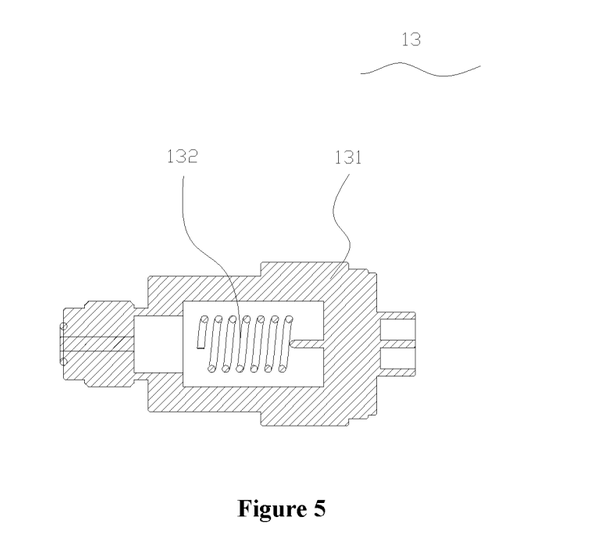
FIG. 5 is a cross-sectional view of the reference electrode in FIG. 1.
Figure 6:
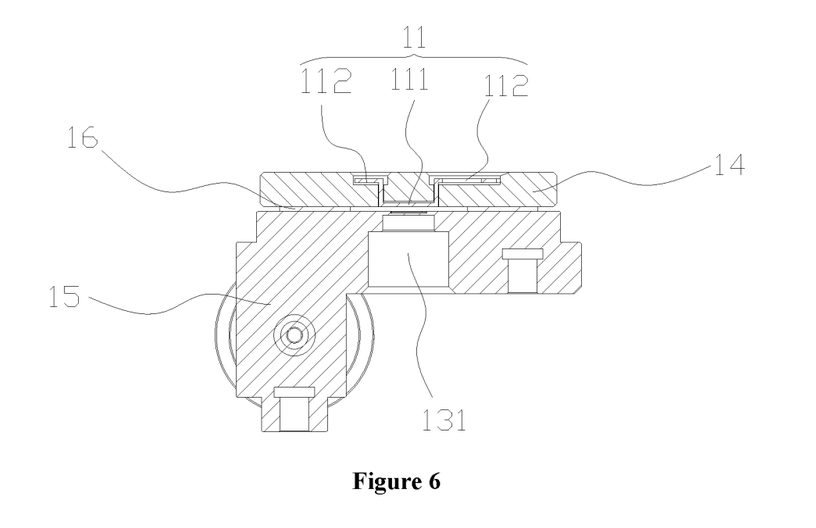
FIG. 6 is a cross-sectional view of FIG. 2 in the direction of A-A.
Figure 7:
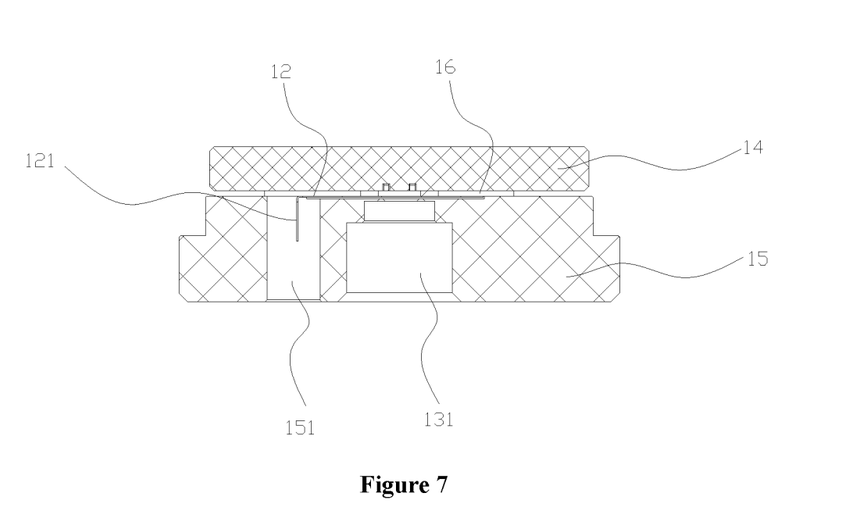
FIG. 7 is a cross-sectional view of FIG. 2 in the direction of B-B.

Reference is made to FIGS. 1 to 6, wherein, FIG. 1 is the structure representation of flow-through cell unit; FIG. 2 is a front view of FIG. 1; FIG. 3 is a bottom view of FIG. 1; FIG. 4 is a structure representation of FIG. 1 after the upper plate is removed; FIG. 6 is a cross-sectional view of FIG. 2 in the direction of A-A; FIG. 7 is a cross-sectional view of FIG. 2 in the direction of B-B.

In one specific example, the present disclosure provides a flow-through cell unit 1 for electrochemiluminescence immune system. The test liquid containing magnetic bead coated antibody-antigen-luminescence agent undergoes electrochemiluminescence reaction in the flow-through cell unit 1. The flow-through cell unit comprises a working electrode 12 and a counter electrode 11, and the working electrode 12 and the counter electrode 11 are arranged one above the other. In addition, the flow-through cell unit 1 also comprises a reference electrode 13, which, together with the working electrode 12 and the counter electrode 11, constitutes a triple-electrode system. The working electrode 12 and the counter electrode 11 form a reaction circuit, and the working electrode 12 and the reference electrode 13 form a detection circuit.

In the present example, the working electrode 12 and the counter electrode 11 are arranged one above the other. When the flow-through cell unit is cleaned, the cleaning liquid does not need to cycle around the two electrodes, which is convenient to clean and has no dead angle, so that the cleaning effect is better, avoiding the aging of electrode caused by poor cleaning, prolonging the service life of flow-through cell unit, and greatly improving the accuracy of a measurement result. Meanwhile, the working electrode 12 and counter electrode 11 arranged one above the other makes the components in the flow-through cell unit arranged tightly, sparing the floor space and decreasing the production cost.

Specifically, as shown in FIG. 4, the counter electrode 11 comprises two needle electrodes disposed above the working electrode 12 which is a sheet electrode. In operation, the two needle electrodes apply the voltage at the same time, jointly form cathode for electrochemiluminescence reaction, and form reaction circuit with the working electrode 12, so that the current of the working electrode 12 is continuous, ensuring the occurrence and recurrence of electrochemiluminescence reaction on the working electrode 12, while exerting no effect on the reaction on the working electrode 12.

In the present example, the working electrode 12 is a rectangular sheet electrode with a smooth surface. When the test liquid containing magnetic bead coated with antibody-antigen-luminescence agent flows through, more test liquid can be attached to the surface of the working electrode 12 and distributed evenly. When the electrochemiluminescence reaction takes place, the efficiency of the electrochemiluminescence reaction is improved. When detection is carried out after the reaction, the evenly distributed analyte is easy to be controlled, improving the accuracy of measurement result.

At the same time, the counter electrode 11 is needle electrode connecting to a photomultiplier on top of it, through which the photons generated on the working electrode 12 is measured. Therefore, the needle-shape counter electrode 11 can avoid the blocking of optical path between the working electrode 12 and the photomultiplier tube, ensuring the accuracy of measurement. In addition, in order to ensure the counter electrode 11 has a large enough area, the counter electrode 11 comprises two needle electrodes working together.

In addition, the counter electrode 11 and the working electrode 12 are disposed inside the flow-through cell, which has liquid flow path for the liquid to flow through. The reference electrode 13 is disposed on one side of the flow-through cell, wherein the working electrode 12, the counter electrode 11 and the reference electrode 13 are in fluid communication through liquid flow path therebetween, and wherein the reference electrode 13 comprises a third working section 132 which is in fluid communication with the liquid flow path and its communication side with the liquid flow path is provided with a porous structure, which prevents the liquid with acid-base components in the liquid path erodes the reference electrode 13 under the premise of signal connectivity.

The third working section 132 is hold in a housing 131 of the reference electrode. In addition, conductive solution, such as potassium chloride or sodium chloride, is also contained in the housing 131 of the reference electrode. In order to prevent the oxidation of the third working section 132 caused by long-term use, the third working section 132 needs to be immersed in the conductive solution for a long time. Therefore, in order to ensure the third working section can be immersed in the conductive solution when there is less conductive solution in the housing 131 of the reference electrode, the third working section 132 is designed to be in spiral shape (as shown in FIG. 5), or an electrode with a cross section of waveform, triangle or other shapes is provided, so that the oxidation of the third working section 132 is efficiently prevented, making the reference value stable and reliable during assay, and further improving the accuracy of a measurement result and increasing the service life of the flow-through cell unit.

In practice, the structures of the working electrode 12, the counter electrode 11 and the reference electrode 13 are not limited to the above. The cross-section of the working electrode 12 can also be any other geometrical shapes such as circle or polygon. The cross-section of the counter electrode 11 can also be any other geometrical shapes such as sheet or spiral, and the third working section 132 of the reference electrode 13 can also be a conventional needle electrode in the art. However, based on the purpose of improving efficiency of the electrochemiluminescence reaction without affecting signal collection and preventing electrode oxidation, the structures of the working electrode 12, the counter electrode 11 and the reference electrode 13 are preferred to be the structures in the example.

In addition, the working electrode 12, the counter electrode 11 and the reference electrode 13 can be made from materials such as gold, platinum, graphite, silver, silver chloride and so on. Because platinum has relative good extensibility and can be processed into variety of shapes, thus, in order to improve the flexibility of the electrode structures, platinum electrode are preferred in the example. The porous structure at the connection surface between the third working section 132 and the liquid flow path can be conventional porous structure such as porous ceramic and so on.

Further, as shown in FIGS. 1 to 6, the flow-through cell unit 1 also comprises an upper plate 14 and a lower plate 15, which match each other and form the flow-through cell unit. Therein, the upper plate 14 is made of transparent optical glass, through which the light emitted by electrochemiluminescence reaction transfers. At the same time, the counter electrode 11 is fixed to the upper plate 14, the working electrode 12 is fixed to the lower plate 15. There is a vertical gap between the working electrode 12 and the counter electrode 11, which forms the liquid flow path between the working electrode 12 and the counter electrode 11.

As shown in FIG. 4, the flow-through cell unit 1 further comprises a gasket 16 set on the surface of the working electrode 12, on which a first through hole 161 is provided. The first through hole 161, the lower plate 15 and the upper plate 14 form a reaction chamber, which is sealed by the gasket 16, thus preventing liquid leakage. At the same time, the first through hole 161 is in a spindle shape with a cross-section of two small ends and a big middle. In addition, a liquid inlet and a liquid outlet are respectively disposed at the two ends of the spindle-shaped first through hole 161, and the test liquid and rinsing liquid flow through the spindle-shaped reaction chamber.

In the example, the spindle-shaped reaction chamber has a small volume so that when test liquid and rinsing liquid flow in the reaction chamber, the fluid flows nearly in a straight line, without whirling. Therefore, the test liquid can sufficiently contact with the working electrode 12 and the counter electrode 11 during reaction, being helpful for the reaction to proceed smoothly. More importantly, when the electrode is subjected to rinsing, the rinsing liquid flows in from the liquid inlet and flows out from the liquid outlet smoothly. The cleaning liquid flows almost in a straight line inside the reaction chamber and rinse without dead angle, thereby efficiently preventing the electrode from aging.

It is understood that the first through hole 161 of the gasket 16 is not limited to spindle-shaped structure with two small ends and a big middle, it can also be rectangular structure which has a uniform cross-section area along the direction of fluid flowing. However, when the first through hole 161 is spindle-shaped, the cross-section areas of the liquid inlet and the liquid outlet are smaller compared with other parts, so that the flow rates at the liquid inlet and the liquid outlet increase, making the test liquid and the rinsing liquid flow into and out of the reaction chamber rapidly.

Further, as shown in FIG. 4, the upper plate 14, the gasket 16 and the lower plate 15 have several screw holes, which cooperate with bolts. Therein, some bolts joint the upper plate 14, the gasket 16 and the lower plate 15 together to form the flow-through cell unit 1. Some other bolts join the flow-through cell unit 1 and the detection unit 3 positioned above the flow-through cell unit 1 together. The detection unit 3 measures the light passing through the upper plate 14.

In addition, as shown in FIG. 4, the middle of the gasket 16 is a spindle-shaped structure, in the middle of which the spindle-shaped first through hole 161 is provided. The outer peripheral wall of the first through hole 161 protrudes outward, forming a plurality of arc structures 162, in which the screw holes are provided. In the example shown in FIG. 1, there are 4 screw holes set on the upper plate 14, the lower plate 15 and the gasket 16. Therein, two are used to join the upper plate 14, the lower plate 15 and the gasket 16, the other two are used to join the flow-through cell unit 1 with the detection unit 3. In practice, the number of the screw hole and the position is not limited to this, but can be set according to need, and are not limited herein.

In addition, the shape of the gasket 16 is not limited to this, which can be roundness matching with the upper plate 14 and the lower plate 15. Therein, the spindle-shaped first through hole 161 is provided in the middle of the round structure, and several screw holes are provided on two sides of the first through hole 161. However, the gasket 16 in the example needs the least material, and more important, it maximally decreases light absorption by the gasket 16, so that improving the accuracy of the measurement results.

On the other hand, as shown in FIG. 4, the counter electrode 11 comprises a first working section 111, working electrode 12 comprises a second working second 122, and the first working section 111 and the second working section 122 form a reaction circuit. In addition, the area of the second working section 122 is less than that of the first through hole 161. Setting in this way further makes the size of the components in the flow-through cell unit 1 smaller, helping to miniaturize the device.

Meanwhile, the first working section 111 is connected to a first hook 112 extending along the direction to the upper plate 14. Correspondingly, a first hook groove matching the first hook 112 is set on the upper plate 14. The first hook 112 is clipped to the first hook groove so that the counter electrode 11 is fixed to the upper plate 14.

Particularly, as shown in FIG. 4 and FIG. 5, two ends of the first working section 111 bend along the direction to the upper plate 14, forming two first hooks 112. Two first hook grooves matching the first hook 112 are set on the upper plate 14. The first hook 112 is invers "L" type hook, correspondingly, the first hook groove is invers "L" type hook groove matching with the invers "L" type hook.

Since the counter electrode 11 is two needle electrodes and the material of which is usually platinum, it can be bent and folded to a variety of shapes. When it is fixed to the upper plate 14, the two ends is bent to form an inverse "L" type hook, making the counter electrode 11 firmly fixed to the upper plate 14, so that ensures the stability of the electrochemiluminescence reaction.

Further, as shown in FIG. 2, a groove 17 is provided at the outer periphery of the upper plate 14 and the lower plate 15. The two first hook grooves extend upward to upper surface of the upper plate 14, and any one of the two first hook grooves extends to the groove 17, so that one end of the counter electrode 11 extends to the groove 17, through which the counter electrode 11 contacts with an outer power source that apply voltage to the counter electrode 11.

In the example shown in FIG. 4 and FIG. 6, the working electrode 12 is perpendicular to the first through hole 161 of the gasket 16. The second working section 122 bends downward the direction of lower plate 15 to form a second hook 121. Correspondingly, a second through hole 151 matching with the second hook 121 is provided on the lower plate 15, and the second hook 121 is clipped to the second through hole 151, so that the working electrode 12 is fixed to the upper surface of the lower plate 15. In addition, through the second through hole 151 the second hook 121 contacts with outer power source which applies voltage to the working electrode 12.

It is understood that the shape of the first hook 112 and the second hook 121 is not limited to this, and it can be any other conventional shape in the art, as long as it realizes the connection between the counter electrode 11 and the upper plate 14 as well as the counter electrode 12 and the lower plate 15. In practice, the connections between the counter electrode 11 and the upper plate 14 as well as the working electrode 12 and the lower plate 15 are not limited to clipping, and it can be any other connection type in the art. Thus, there is no restriction to the connection type and shape and position of the two hooks.

In addition, the lower plate 15 and the housing 131 of the reference electrode in the example are made from anticorrosive peek material to protect the electrodes.

Figure 8:
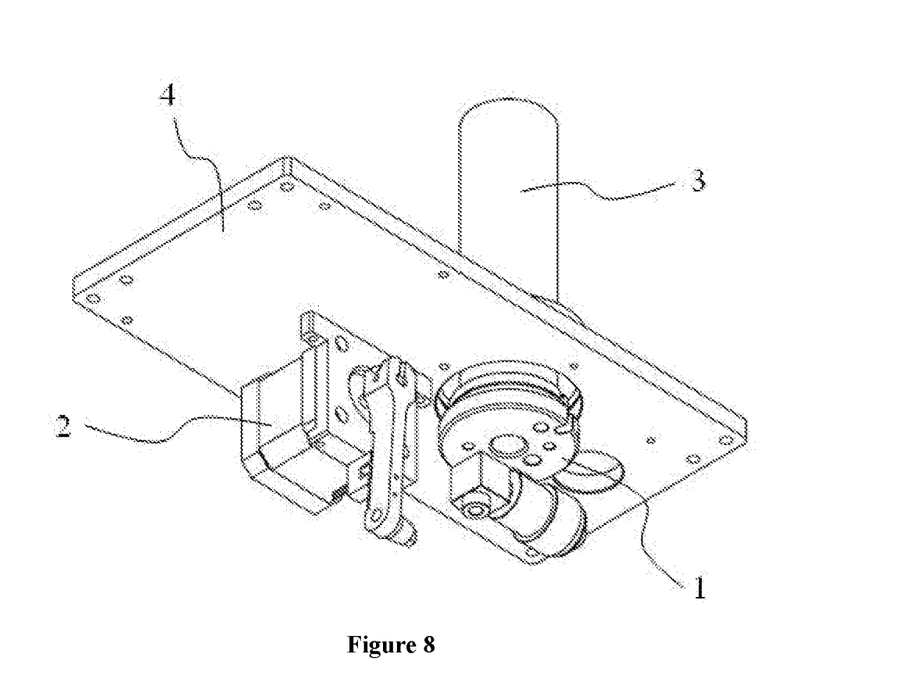
FIG. 8 is a structure representation of the electrochemiluminescence immunoassay system provided by the present disclosure.
Figure 9:
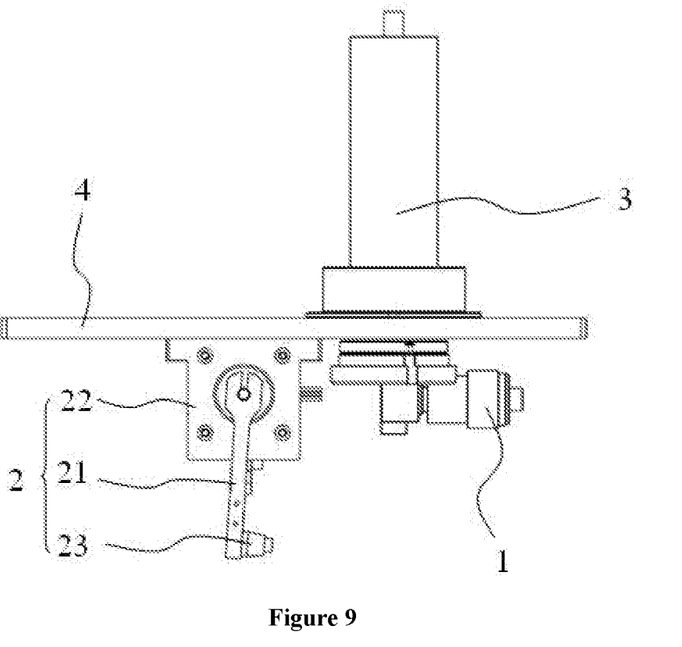
FIG. 9 is the front view of FIG. 8.

Please continue to refer to FIGS. 7 and 8, therein, FIG. 8 is a structure representation of the electrochemiluminescence immunoassay system provided by the present disclosure; FIG. 9 is the front view of FIG. 8.

As shown in FIG. 8 and FIG. 9, the present disclosure provides an electrochemiluminescence immunoassay system, comprising the flow-through cell unit 1 and a detection unit 3 for analyzing the flow-through cell unit 1, also comprising a control unit 2 for controlling the flow-through cell unit 1 and a fixed base 4 for fixing the flow-through cell unit 1 and the control unit 2, wherein the flow-through cell unit 1 is the flow-through cell unit 1 in any one of the above-mentioned examples. Since the flow-through cell unit 1 has the technical effects mentioned above, the electrochemiluminescence immunoassay system comprising the flow-through cell unit 1 also has the same technical effects, which is not repeated herein.

Therein, as shown in FIG. 7 and FIG. 8, the control unit comprises a rotating arm 21, and one end of the rotating arm 21 is connected to a stepper motor 22 via hinge, and the other end of the rotating arm 21 is connected to a magnet 23. Correspondingly, a groove is provided at the bottom of the lower plate of the flow-through cell unit 1. When the rotating arm 21 rotate to the groove under the control of the stepper motor 22, the magnet 23 moves into the groove, under the working electrode 12 and manipulates the magnetic beads in the test liquid to be attached to the working electrode 12 so that initiate the electrochemiluminescence reaction. In addition, in order to ensure sufficient magnetic beads being attached to the working electrode 12, the magnet 23 is a permanent magnet.

In practice, the control unit 2 does not have to be realized by the stepper motor 22 through controlling the rotating arm 21, while it can also be a conventional crank connecting-rod mechanism in the art. However, the control unit 2 in the example can strictly control the motion trajectory of the rotating arm 21 through the stepper motor 22, therefore improving the accuracy of the device.

When the electrochemiluminescence immunoassay system operates, firstly, the rotating arm 21 is rotated to the underneath of the working electrode 12 under the control of the stepper motor 22 of the control unit 2; the test liquid is attached to the surface of the sheet working electrode 12 by the magnet 23 on the rotating arm 21; complex bound with a marker, i.e. ruthenium, is separated from the free marker under magnetic field. Meanwhile, a solution containing TPA or DBAE (dibutylamino-ethanol) is added, and voltage is applied to start the ECL reaction. Luminescent substrate pyridine ruthenium (II) and TPA lose an electron and are oxidized to pyridine ruthenium (III) and cation excited state TPA+ on the surface of the working electrode 12. At the same time, cation excited state TPA+ removes one proton and becomes excited TPA with strong reducibility. The pyridine ruthenium (III) with strong oxidizability and the excited state TPA with strong reducibility undergo oxidation-reduction reaction, so that the pyridine ruthenium (III) is reduced to excited pyridine ruthenium (II). The excited pyridine ruthenium (II) decays in a fluorescent mechanism, releases energy by emitting a 620 nm photon and becomes the ground state luminescent substrate pyridine ruthenium (II).

This process repeats on the surface of electrode, producing a lot of photons. The light intensity is measured by the photomultiplier tube in the detection unit 3 and then amplified and analyzed by a computer. Therein, the light intensity is linearly related to the concentration of pyridine ruthenium, and the concentration of the antigen in the test liquid is converted based on the light intensity emitted by the pyridine ruthenium on the working electrode 12. The principle of the DBAE reaction system is the same as that of the TPA reaction system described above.

In the foregoing, an electrochemiluminescence immunoassay system provided by the present disclosure and a flow-through cell unit thereof are described in detail. Specific examples are used herein to describe the principles and implementation manners of the present disclosure, and the description of the example is merely intended to help understand the method and core ideas of the present disclosure. It should be noted that one of ordinary skill in the art can make various improvements and modifications to the present disclosure without departing from the principle of the present invention, and such improvements and modifications fall into the protection scope of the claims of the present invention.

What is claimed is:

1. A flow-through cell unit of an electrochemiluminescence immunoassay device comprising a working electrode (12), a counter electrode (11) and a reference electrode (13), wherein the counter electrode (11) comprises a first working section (111), the working electrode (12) comprises a second working section (122), and the first working section (111) and the second working section (122) form a reaction circuit;

the flow-through cell unit is formed by an upper plate (14) and a lower plate (15) matching each other, wherein the upper plate (14) is made of transparent material, the counter electrode (11) is fixed to the upper plate (14), and the working electrode (12) is fixed to the lower plate (15), the working electrode (12) and the counter electrode (11) are arranged one above the other, the working electrode (12), the counter electrode (11) and the reference electrode (13) are in a fluid communication path, the reference electrode (13) comprises a third working section (132), and a porous structure is provided between the working section (132) and the fluid communication path; and a gasket (16) having a first through hole (161) is provided between the upper plate (14) and the lower plate (15), wherein the first through hole (161), the lower plate (15) and the upper plate (14) form a reaction chamber, wherein a liquid inlet and a liquid outlet are provided in the lower plate (15) under the reaction chamber, and wherein a test liquid undergoes electrochemiluminescence reaction in the reaction chamber.

2. The flow-through cell unit according to claim 1, wherein screw holes in communication with each other are provided in the upper plate (14), the gasket (16) and the lower plate (15).

3. The flow-through cell unit according to claim 1, wherein at least one end of the first working section (111) bends along the direction to the upper plate (14) to form a first hook (112), a first hook groove matching the first hook (112) is provided in the upper plate (14), and the first hook (112) is clipped to the first hook groove;

at least one end of the second working section (122) bends along the direction to the lower plate (15) to form a second hook (121), a second through hole (151) matching the second hook (121) is provided on the lower plate (15), and the second hook (121) is clipped to the second through hole (151).

4. An electrochemiluminescence immunoassay system, comprising a flow-through cell unit (1) according to claim 1, and an detection unit (3) for detecting an optical signal in the flow-through cell unit (1), a control unit (2) for controlling the operation of the flow-through cell unit (1), and a fixing plate (4), wherein the flow-through cell unit (1) and the control unit (2) are fixed on the fixing plate.

5. The electrochemiluminescence immunoassay system according to claim 4, wherein the control unit (2) comprises a rotating arm (21) and a stepper motor (22), wherein one end of the rotating arm (21) is hinged to the stepper motor (22) for controlling the rotation of the rotating arm (21), and wherein the other end of the rotating arm (21) is connected to a magnet (23) for controlling the attraction of magnetic beads in a test liquid to the working electrode (12).

6. The flow-through cell unit according to claim 1, wherein the counter electrode (11) comprises two needle electrodes disposed above the working electrode (12), and the working electrode (12) is a sheet electrode.

\* \* \* \* \*